United States Patent [19]
Takahashi et al.

[11] Patent Number: 6,087,541
[45] Date of Patent: Jul. 11, 2000

[54] POLYENE ALCOHOL DERIVATIVE AND PROCESS FOR PRODUCING THE SAME

[75] Inventors: Toshiya Takahashi, Ibaraki; Yasunobu Miyamoto, Oita, both of Japan

[73] Assignee: Sumitomo Chemical Company, Limited, Osaka, Japan

[21] Appl. No.: 09/086,542

[22] Filed: May 29, 1998

[30] Foreign Application Priority Data

May 29, 1997 [JP] Japan ................................. 9-140006

[51] Int. Cl.$^7$ .......................... C07C 27/10; C07C 35/18; C07C 315/00
[52] U.S. Cl. ............................ 568/700; 568/28; 568/824
[58] Field of Search ................. 568/700, 28, 824

[56] References Cited

U.S. PATENT DOCUMENTS

| | | | |
|---|---|---|---|
| 4,211,782 | 7/1980 | Vane ....................................... | 568/700 |
| 5,902,738 | 5/1999 | Orsat et al. ............................ | 568/700 |

FOREIGN PATENT DOCUMENTS 8812204  12/1998  European Pat. Off. .

OTHER PUBLICATIONS

EP–98–10–9798, European Search Report. (Aug. 19, 1998).
XP–002074899, Chemistry Letters, pp. 1009–1012, published by Chemical Society of Japan, 1977.
XP–002074900, Research Article, pp. 1101–1110, published by Chemical Research Laboratories, 1978.
XP–002074901, Research Article, pp. 761–769, published by Yokohama National University, 1981.
XP–00237120, Research Article, pp. 1130–1136, published by Nagoya University, 1991.
XP–002074898, Research Article (in French), pp. 746–750, published by Laboratory of Synthesized Natural Products, 1972.

*Primary Examiner*—Louise N. Leary
*Attorney, Agent, or Firm*—Birch, Stewart, Kolasch & Birch, LLP

[57] ABSTRACT

There is disclosed a novel polyene alcohol derivative of the formula [I]:

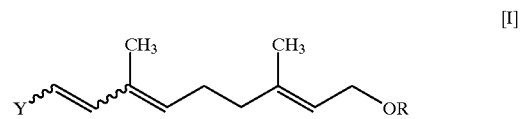

wherein, R represents a hydrogen atom or a protective group for a hydroxy group, and Y represents the following group:

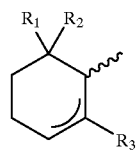

or

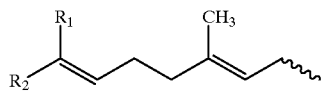

wherein, R represents a hydrogen atom or a protective group for a hydroxy group, and Y represents the following group, and a production method thereof.

8 Claims, No Drawings

POLYENE ALCOHOL DERIVATIVE AND PROCESS FOR PRODUCING THE SAME

BACKGROUND OF THE INVENTION

Field of the Invention

The present invention relates to a novel polyene alcohol derivative that is useful as an intermediate of a medicine, for example, an intermediate of Retinol (vitamin A), and a method for producing the same.

SUMMARY OF THE INVENTION

The present invention provides:
1. a polyene alcohol derivative of the formula [I]

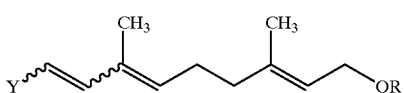
[I]

wherein, R represents a hydrogen atom or a protective group for a hydroxy group, and
Y represents the following group:

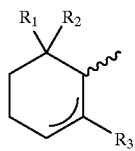

or

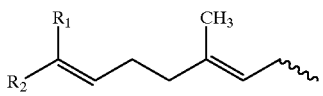

wherein, $R^1$, $R^2$ and $R^3$ may be the same or different and represent a hydrogen atom or an alkyl group having 1 to 3 carbon atoms;

2. a method for producing the polyene alcohol derivative of the formula [I] as defined in claim 1, which comprises reacting a sulfone compound of the formula [II]:

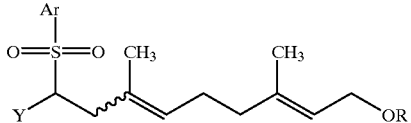
[II]

wherein, R and Y are the same as defined in claim 1, and Ar represents an aryl group which may be substituted, with a base.

3. a sulfone compound of the formula [II] as defined above; and 4. a method for producing the sulfone compound of the formula [II] as defined above, which comprises reacting a compound of the formula [III]:

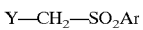
[III]

wherein, Ar and Y are the same as defined above, with a halide compound of the formula [IV]:

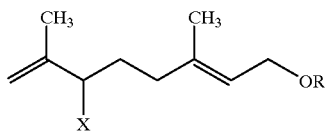
[IV]

wherein, R is the same as defined above, and X represents a halogen atom, in the presence of a basic compound.

DETAILED DESCRIPTION OF THE PREFERRED EMBODIMENTS

First description will be made to the first aspect of the present invention which relates to the polyene alcohol derivative of the formula [I].

In the formula [I], as for the protective group for a hydroxy group, Protective Groups in Organic Synthesis, Greene and Wuts, 2nd Edition, (1992), John Wiley & Sons, Inc., the disclosure of which is incorporated herein by reference.

Examples of the protective group for a hydroxy group include: an acyl group such as an acetyl, pivaroyl, benzoyl, or p-nitrobenzoyl group, a silyl group such as a trimethylsilyl, t-butyldimethylsilyl, or t-butyldiphenylsilyl, an alkoxymethyl group such as tetrahydropyranyl, methoxymethyl, methxyethoxymethyl, or 1-ethoxyethyl group, t-butyl, trityl, benzyl, p-methoxybenzyl, trichloroethoxycarbonyl, allyloxycarbonyl group.

In the formula [I], $R^1$, $R^2$ and $R^3$ may be the same or different and represent a hydrogen atom or an alkyl group having 1 to 3 carbon atoms, examples of which include a methyl, ethy, n-propyl and i-propyl group.

The following group in Y:

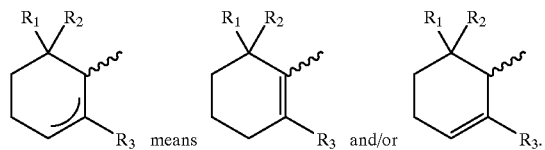

The polyene alcohol derivative of the formula [I] of the present invention can be obtained by the method of reacting a sulfone compound of the formula [II] as defined above with a base.

In the formula [II] above, Ar represents an aryl group which may be substituted, examples of which include: a phenyl, naphthyl, and the pheny or naphthyl group may be substituted with a $C_1$–$C_5$ lower alkyl group (e.g., methyl, ethyl, n-propyl, i-propyl, n-butyl, i-butyl, s-butyl, t-butyl, n-pentyl, neopentyl, t-amyl) a $C_1$–$C_5$ lower alkoxy group (e.g., methoxy, ethoxy, n-propoxy, i-propoxy, n-butoxy, i-butoxy, s-butoxy, t-butoxy, n-pentoxy, neopentoxy, t-amyloxy, a halogen atom(e.g., chlroine, bromine, iodine, flurrine), a nitro group and the like.

Specific examples of the Ar includes: phenyl, naphthyl, o-tolyl, m-tolyl, p-tolyl, o-methoxyphenyl, m-methoxyphenyl group, p-methoxyphenyl group, o-chlorophenyl group, m-chlorophenyl group, p-chlorophenyl group, o-bromophenyl group, m-bromophenyl group, p-bromophenyl group, o-iodophenyl group, m-iodophenyl group, p-iodophenyl group, o-fluorophenyl group, m-fluorophenyl group, p-fluorophenyl group, o-nitrophenyl group, m-nitrophenyl group, and p-nitrophenyl group.

Examples of the base to be used in the method include an alkali metal hydride, an alkaline earth metal hydride, an alkali metal alkoxide, an alkaline earth metal alkoxide, an alkali metal hydroxide, an alkaline earth metal hydroxide, and an alkali metal amide.

Specific examples thereof include the alkali metal hydride such as sodium hydride, potassium hydride, the alkaline earth metal hydride such as calcium hydride, the alkali metal alkoxide such as sodium methoxide, potassium methoxide, potassium t-butoxide, the alkali metal hydroxide such as sodium hydroxide and the like, the alkaline earth metal hydroxide.

The amount of the base is usually from approximately 2 to 20 mols per mol of the sulfone compound [II].

In the above-described reaction, a solvent is usually used. The solvent that can be used in the reaction and the amount thereof is not specifically limited and includes, for example, a hydrocarbon solvent such as aliphatic hydrocarbon (e.g., n-hexane, cyclohexane, n-pentane), and aromatic hydrocarbon (e.g., toluene and xylene), an ether solvent such as diethyl ether, tetrahydrofuran, and anisole, a halogenated hydrocarbon solvent such as chloroform, dichloromethane, dichloroethane and monochlorobenzene, and an aprotic polar solvent such as DMF, DMSO, N,N-dimethylacetamide, hexamethylphosphoric triamide.

The reaction temperature is usually in the range from approximately from −78° C. to the boiling point of the solvent employed in the reaction.

After completion of the reaction, the polyene alcohol derivative [I] can be isolated and/or purified by a conventional post-treatment method, for example, such as extraction, distillation and chromatographies, if necessary.

Deblocking of the protective group of the obtained compound can be effected according to a conventional method as described in Protective Groups in Organic Synthesis, Greene and Wuts, 2nd Edition, (1992), John Wiley & Sons, Inc by selecting appropriate conditions. Deblocking of the protective group also may be effected at the same time by appropriately selecting a post treatment condition after completion of the reaction.

The polyene alcohol derivative [I] or the sulfone compound [II] in the present invention may take any of an E or Z geometric isomeric form, optically active form and a racemic form, or may be a mixture thereof.

The sulfone compound [II] can be obtained by the method which comprises reacting the compound of the formula [III] as defined above, with a halide compound of the formula [IV] as defined above in the presence of a basic compound.

In the compound of the formula [III], examples of Ar also include those for Ar in the formula [II].

Examples of R in the halide compound of the formula [IV] include those for R in the sulfone of the formula [II] above.

Examples of the halogen atom X include a chlorine atom, bromine atom, iodine atom and the like.

In this method any basic compound that can generate an anion of the compound [III] can be used. Among the basic compound to be used in this reaction, Grignard reagent such as alkylmagnesium halide, alkyl lithium are preferably used.

The amount used of such a base is usually from approximately 1 to 3 moles per mol of the compound [III].

The basic compound includes an alkyl lithium, Grignard reagent, an alkali metal hydroxide, an alkaline earth metal hydroxide, an alkali metal hydride, an alkaline earth metal hydride, an alkali metal alkoxide and an alkaline earth metal alkoxide.

Specific examples of the basic compound include n-butyl lithium, s-butyl lithium, t-butyl lithium, ethyl magnesium bromide, ethyl magnesium chloride, sodium hydroxide, potassium hydroxide, sodium hydride, potassium hydride, sodium methoxide, potassium methoxide and potassium t-butoxide.

Grignard reagent such as alkyl magnesium halide and alkyl lithium are preferably used in this reaction.

The amount of the basic compound to be used is usually 1 to 3 moles per mol of the compound [III].

An organic solvent is ususally used in this reaction. Examples of the organic solvents are an ether solvent such as diethyl ether, tetrahydrofuran and anisole, a hydrocarbon solvent such as n-hexane, cyclohexane, n-pentane, toluene and xylene, a halogenated hydrocarbon solvent such as chloroform, dichloromethane, dichloroethane, monochlorobenzene and o-dichlorobenzene, and a aprotic polar solvent such as N,N-dimethylformamide, dimethylsulfoxide, N,N-dimethyl acetamide and hexamethyl phosphoric triamide.

The basic compound is contacted with the compound [III] usually in the range from about −78° C. to 50° C. When an alkyl lithium is used, the temperature is usually in the range from about −78° C. to 0° C. and when other reagent is used, usually in the range from about −30° C. to 50° C.

After contacting the basic compound with the compound [III], a zinc compound may be added to the resulting reaction mixture to enhance the reactivity. The zinc compound is usually contacted with the resulting mixture in a temperature range of −78° C. to 20° C., preferably −20° C. to 0° C.

Examples of the zinc compound include zinc halogenide, zinc oxide, zinc sulfide, zinc hydroxide, zinc carboxylate, zinc nitrate, zinc sulfate, zinc carbonate, zinc sulfonate, zinc phosphate, zinc thiocyanate, zinc chromate, zinc perchlorate, zinc alkoxide, zinc cyanide and zinc acetylacetonate. Preferably, zinc halide such as zinc chloride($ZnCl_2$), zinc bromide($ZnBr_2$) or zinc iodide($ZnI_2$) is used. The amount of the zinc compound to be used is usually 0.1 to 2 moles per mol of the basic compound.

In this reaction, a metal catalyst may be further added. Examples of the metal catalysts include metal compounds of copper, manganese, iron, nickel, cobalt, silver, chromium, and zinc.

Examples of the metal compounds include halogenide, oxide, sulfide, hydroxide, carboxylate, nitrate, sulfate, carbonate, sulfonate, phosphate, thiocyanate, chromate, perchlorate, alkoxide, cyanide, acetylacetonate and a complex of said metal, for example, a complex having a phosphorous ligand or dimethyl sulfide such as triarylphosphino complex or cuprous halide dimethyl sulfide complex.

Specific examples of the metal compound include cuprous chloride, cupric chloride, cuprous bromide, cupric bromide, cuprous iodide, cuprous oxide, cupric oxide, copper sulfide, copper acetate, copper nitrate, copper sulfate, copper carbonate, copper hydroxide, copper cyanide, copper acetylacetonate, copper phosphate, copper thiocyanate, copper chromate, copper perchlorate, copper methoxide, manganese chloride, manganese acetate, manganese carbonate, manganese nitrate, manganese sulfate, manganese acetylacetonate, cobalt chloride, nickel chloride, ferrous chloride, ferric chloride, iron oxides and silver oxide. Copper compound are preferably used.

The amount of the metal compound to be used is usually 0.01 to 1 mol, preferably, 0.05 to 0.2 mol per mol of the compound [III]. The metal compound is usually added to the reaction mixture in a temperature range of −78° C. to 20° C., preferably −20° C. to 0° C.

The halide compound [IV] is then usually reacted with the resulting reaction mixture at a temperature of −10° C. to 70° C.

After completion of the reaction, the sulfone compound of the formula [II] are isolated and/or purified by a conventional post-treatment, and may be further purified by silica gel chromatography, if necessary.

In the present invention, the compound of the formula [III] and the halide compound of the formula [IV] can be readily synthesized by known methods (Yukagaku, 44(4), 316–21, 1995, Yukagaku, 39(2), 83–9, 1990, Tetrahedron Letters, 41(24), 5741–6, 1986).

The halide compound of the formula [IV] may be used in the reaction, its hydroxy group being protected or not. The protective group can be introduced by a conventional method as described in Protective Groups in Organic Synthesis, Greene and Wuts, 2nd Edition, (1992), John Wiley & Sons, Inc.

For example, an acetyl group can be introduced by reacting with acetic anhydride at room temperature or lower in the presence of zinc chloride or under reflux in acetic anhydride.

The polyene alcohol derivative of the present invention [I] is useful as a medicine, for example, an intermediate of vitamin A.

EXAMPLE

The following examples further illustrate the present invention but it is not construed to limit the scope thereof. Preparation of 6-chloro-3,7-dimethyl-octa-2,7-dien-1-yl acetate 40 g (0.204 mol) of geranyl acetate was dissolved in hexane, to this solution was added gradually 17.1 g (0.071 mol) of trichloroisocyanuric acid, and the mixture was kept at from −10° C. to 0° C. After the reaction, excess trichlorocyanuric acid and isocyanuric acid by-produced were removed from the reaction mixture by filtration. The filtrate was washed with sodium hydrogen carbonate and water in sequence, dehydrated with anhydrous magnesium sulfate, then, a crude product was obtained by evaparating the solvent.

The resulted crude product was purified by silica gel column chromatography, to obtain the desired halide compound, 6-chloro-3,7-dimethylocta-2,7-dien-1-yl acetate in a yield of 85.5%.

Example 1

5.85 g (20 mmol) of β-cyclogeranyl-p-tolylsulfone [1-methyl-4-(2,6,6-trimethyl-cyclohex-1-enylmethanesulfonyl)-benzene] was dissolved in 60 ml of THF, the solution was cooled to −60° C. or lower, then 12.5 ml (20 mmol) of n-butyl lithium was slowly added dropwise into the solution through a syringe under nitrogen atmosphere. After the addition, the solution was allowed to stand at an ambient temperature and kept at 0° C., and then stirred for 3 hours at the same temperature.

Then, the solution was cooled to −15° C., and 2.05 g (15 mmol) of zinc chloride was quickly added, and the solution was stirred for 2 hours. Then, 0.4 g (2 mmol) of cuprous bromide dimethyl sulfide complex (Me$_2$S·CuBr) was added and the mixture was stirred for 1 hour.

To this mixture was added dropwise 3.46 g (15 mmol) of 6-chloro-3,7-dimethylocta-2,7-dien-1-yl acetate obtained above at −10° C., to 0° C., and the mixture was stirred for 2 hours at the same temperature, then the mixture was stirred for 6 hours at 60° C. Disappearance of the raw materials was monitored by TLC, post-treatment was conducted according to a conventional method, to obtain a crude product. The resulted crude product was purified by silica gel chromatography, and the desired compound [1-acetoxy-3,7-dimethyl-9-(p-toluenesulfonyl)-9-(2,6,6-trimethyl-cyclohexen-1-yl)-nona-2,6-diene] was obtained as a pale yellow oil in a yield of 85%.

$^1$H-NMR δ (CDCl$_3$) 0.85(3H,s), 1.08(3H,s), 1.20(3H,s), 1.22–1.62(4H,m), 1.68(3H,s), 1.97(2H,s, 2.02(2H,s);2.06 (3H,s), 2.43(3H,s), 2.55–2.98(2H,m), 3.89(1H,t, J=9Hz), 4.59(2H, d, J=9Hz), 5.12(1H, Br ), 5.31(1H,t, J=9Hz), 7.29(2H, d, J=8Hz), 7.75(2H, d, J=8Hz). $^{13}$C-NMR δ (CDCl$_3$) 15.4, 16.3, 18.9, 20.9, 21.4, 22.8, 26.0, 28.1, 29.0, 34.4, 35.4, 39.0, 39.6, 40.9, 61.1, 65.5, 118.3, 127.9, 129.2, 130.1, 130.8, 137.3, 138.7, 141.6, 143.8, 170.9.

Example 2

5.85g (20 mmol) of geranyl-p-tolylsulfone [1-(3,7-dimethyl-octa-2,6-diene-1-sulfonyl)-4-methyl-benzene] was dissolved in 60 ml of THF, the solution was cooled to −60° C. or lower, then 12.5 ml (20 mmol) of n-butyl lithium was slowly added dropwise into the solution through a syringe under nitrogen atmosphere. After the addition, the solution was allowed to stand at an ambient temperature and kept at 0° C., and then stirred for 1 hour at the same temperature.

Then, the solution was cooled to −15° C., and 2.05 g (15 mmol) of zinc chloride was quickly added, and the solution was stirred for 2 hours. Then, 0.4 g (2 mmol) of cuprous bromide dimethyl sulfide complex (Me$_2$S·CuBr) was added and the mixture was stirred for 1 hour.

To this mixture was added dropwise 3.46 g (15 mmol) of 6-chloro-3,7-dimethylocta-2,7-dien-1-yl acetate obtained above at −10< C. to 0° C., and the mixture was stirred for 2 hours at the same temperature, then the mixture was stirred for 6 hours at 60° C. Disappearance of the raw materials was monitored by TLC, post-treatment was conducted according to a conventional method, to obtain a crude product. The resulted crude product was purified by silica gel chromatography, and the desired compound [1-acetoxy-3,7, 11,15-tetramethyl-9-(p-toluenesulfonyl)-hexadeca-2,6,10, 14-tetraene] was obtained as a pale yellow oil in a yield of 71%.

$^1$H-NMR δ (CDCl3) 1.14(3H,s), 1.52(3H,s), 1.56(3H,s), 1.62(3H,s), 1.64(3H,s), 1.95(4H,s), 2.03(4H,s), 2.43(3H,s), 2.17–2.89(2H,m), 3.87(1H,d t, J=4,10Hz), 4.56(2H, d, J=9Hz), 4.89(1H,d, J=9Hz), 5.02(1H,s), 5.12 (1H, d, J=9Hz), 5.30(1H, d, J=9Hz), 7.29(2H, d, J=8Hz), 7.75(2H, d, J=8Hz).

$^{13}$C-NMR δ (CDCl$_3$) 15.8, 16.1, 17.5, 20.9, 21.5, 22.8, 25.5, 26.0, 37.4, 39.5, 39.6, 61.1, 63.3, 117.9, 118.3, 123.4, 127.9, 129.5, 130.3, 131.7, 134.8, 141.5, 144.1, 144.8, 170.9.

Example 3

16.54g (34 mmol) of the halide compound obtained in Example 1 was dissolved in 100 ml of DMF and the solution was heated to 80° C. To this was added dropwise 32.8 ml (170 mmol) of 28% sodium methoxide, and the solution was stirred for 8 hours at the same temperature. Disappearance of the raw materials was monitored by TLC, post-treatment was conducted according to a conventional method, to obtain a crude product. The resulted crude product was purified by silica gel chromatography, and 11,12-dihydroretinol [1-hydroxy-3,8-dimethyl-10-(2,6,6-trimethyl-cyclohexenyl)-deca-2,7,9-triene] was obtained as a pale yellow oil in a yield of 76%.

$^1$H-NMR δ (CDCl3) 1.02(6H,s), 1.41–1.48(2H,m), 1.52–1.59(2H,m), 1.60(3H,s), 1.75(3H,s), 2.03(2H,t, J=9Hz), 2.11(2H,t, J=9Hz), 2.21–2.29(2H,m), 4.12(2H,d, J=9Hz), 5.31–5.45(4H, m), 5.97(2H,s)

$^{13}$C-NMR δ (CDCl$_3$) 12.3, 16.2, 19.2, 21.6, 22.8, 26.4, 32.7, 34.1, 39.5, 39.6, 58.9, 123.4, 124.2, 128.2, 129.6, 134.0, 137.6, 139.0.

Example 4

16.54 g (34 mmol) of the compound obtained in Example 1 was dissolved in 100 ml of cyclohexane and the solution was heated to 40° C. To this was added dropwise 11.92 g (170 mmol) of potassium methoxide, and the solution was stirred for 6 hours at the same temperature. Disappearance of the raw materials was monitored by TLC, post-treatment was conducted according to a conventional method, to obtain a crude product. The resulted crude product was purified by silica gel chromatography, and 11,12-dihydroretinol [1-hydroxy-3,8-dimethyl-10-(2,6,6-trimethylcyclohexenyl)-deca-2,7,9-triene] was obtained as a pale yellow oil in a yield of 90%.

What is claimed is:

1. A polyene alcohol derivative of the formula [I]

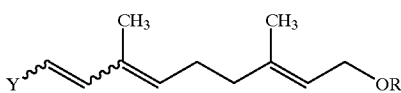

[I]

wherein, R represents a hydrogen atom or a protective group for a hydroxy group, and Y represents the following group:

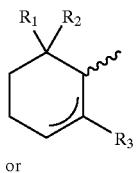

or

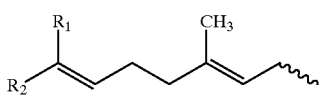

wherein, R$^1$, R$^2$ and R$^3$ may be the same or different and represent a hydrogen atom or an alkyl group having 1 to 3 carbon atoms.

2. A method for producing the polyene alcohol derivative of the formula [I] as defined in claim 1, which comprises reacting a sulfone compound of the formula [II]:

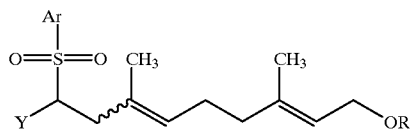

[II]

wherein, R and Y are the same as defined in claim 1, and Ar represents an aryl group which may be substituted, with a base.

3. A method according to claim 2, wherein the base is selected from an alkali metal hydroxide, an alkaline earth metal hydroxide, alkali metal hydride, an alkaline earth metal hydride, an alkali metal alkoxide and an alkaline earth metal alkoxide.

4. A sulfone compound of the formula [II] as defined in claim 2.

5. A method for producing the sulfone compound of the formula [II] as defined in claim 2, which comprises reacting a compound of the formula [III]:

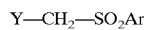

[III]

wherein, Ar and Y are the same as defined in claim 2, with a halide compound of the formula [IV]:

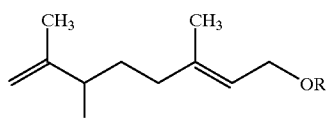

[IV]

wherein, R is the same as defined in claim 2, and X represents a halogen atom, in the presence of a basic compound.

6. The method according to claim 5, wherein the reacting of the compound of the formula [II] with the halide compound of the formula [IV] is conducted in the co-presence of a metal catalyst.

7. The method according to claim 6, wherein the metal catalyst is a copper catalyst.

8. A method for producing the polyene alcohol derivative of the formula [I]

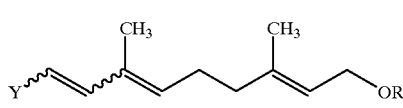

[I]

wherein, R represents a hydrogen atom or a protective group for a hydroxy group, and Y represents the following group:

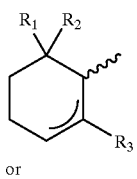

or

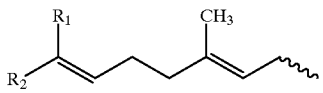

wherein, $R^1$, $R^2$ and $R^3$ may be the same or different and represent a hydrogen atom or an alkyl group having 1 to 3 carbon atoms which comprises reacting a sulfone compound of the formula [II]:

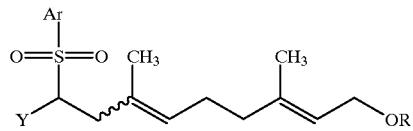

wherein, R and Y are the same as defined in claim 1, and Ar represents an aryl group which may be substituted, with a base wherein the sulfone compound of the formula [II] is obtained by the method of claim 5.

* * * * *

UNITED STATES PATENT AND TRADEMARK OFFICE
CERTIFICATE OF CORRECTION

PATENT NO. : 6,087,541
DATED : July 11, 2000
INVENTOR(S) : Toshiya Takahashi; Yasonubu Miyamoto It is certified that error appears in the above-identified patent and that said Letters Patent is hereby corrected as shown below:

Column 2,
Line 58, "chlroine" should be corrected to read -- chlorine --;

Column 6,
Line 63, "halide" should be corrected to read -- sulfone --;

Column 7,
Lines 5-6, the expression "[1-hydroxy-3, 8-dimethyl-10-(2,6,6- trimethyl-cyclohexenyl)-deca-2,7,9-triene]" should be corrected to read -- [1-hydroxy-3,7-dimethyl-9-(2,6,6-trimethyl-cyclohexenyl)-nona-2,6,8-triene] --; and
Lines 30-31, the expression "[1-hydroxy-3,8-dimethyl-10-(2,6,6-trimethylcyclohexenyl)-deca-2,7,9,-triene]" should read -- [1-hydroxy-3,7-dimethyl-9-(2,6,6-trimethylcyclohexenyl)-nona-2,6,8-triene] --.

Column 7, claim 1,
Lines 47-60, cancel the formulae following the expression in line 46 "Y represents the following group:" and substitute the following formula therefor:

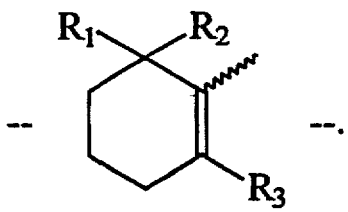

Column 8, claim 6,
Line 49, cancel "[II]" and substitute therefor -- [III] --.

Column 9, claim 8,
Lines 2-15, cancel the formulae and substitute the following formula therefor:

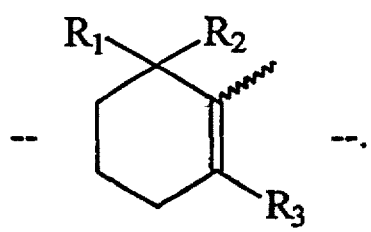

UNITED STATES PATENT AND TRADEMARK OFFICE
CERTIFICATE OF CORRECTION

PATENT NO.   : 6,087,541
DATED        : July 11, 2000
INVENTOR(S)  : Toshiya Takahashi; Yasonubu Miyamoto It is certified that error appears in the above-identified patent and that said Letters Patent is hereby corrected as shown below:

<u>Column 10, claim 8,</u>
Line 11, change the expression "in claim 1" to read -- above --.

Signed and Sealed this

Nineteenth Day of February, 2002

Attest:

JAMES E. ROGAN
*Director of the United States Patent and Trademark Office*

*Attesting Officer*